(12) United States Patent
Colaco et al.

(10) Patent No.: US 6,313,102 B1
(45) Date of Patent: Nov. 6, 2001

(54) METHOD FOR STABILIZATION OF BIOLOGICAL SUBSTANCES DURING DRYING AND SUBSEQUENT STORAGE AND COMPOSITIONS THEREOF

(75) Inventors: Camilo Colaco; Bruce J. Roser; Shevanti Sen, all of Cambridge (GB)

(73) Assignee: Quardrant Holdings Cambridge, Ltd. (GB)

( * ) Notice: Subject to any disclaimer, the term of this patent is extended or adjusted under 35 U.S.C. 154(b) by 0 days.

(21) Appl. No.: 09/389,949

(22) Filed: Sep. 3, 1999

Related U.S. Application Data

(63) Continuation of application No. 08/293,157, filed on Aug. 19, 1994, now Pat. No. 5,955,448.

(30) Foreign Application Priority Data

Apr. 13, 1994 (GB) .................................................. 94073053

(51) Int. Cl.⁷ ...................... A61K 31/715; A61K 31/415; A21D 6/00; A23B 4/03; G01N 31/00
(52) U.S. Cl. ........................... 514/53; 514/391; 514/399; 514/400; 436/18; 426/241; 426/242; 426/443
(58) Field of Search ............................... 514/53, 391, 399, 514/400; 436/18; 426/241, 242, 443

(56) References Cited

U.S. PATENT DOCUMENTS

| | | |
|---|---|---|
| 3,557,717 | 1/1971 | Chivers . |
| 3,619,294 | 11/1971 | Black et al. . |
| 3,632,357 | 1/1972 | Childs . |
| 3,655,442 | 4/1972 | Schwer et al. . |
| 4,127,502 | 11/1978 | Li Mutti et al. . |
| 4,158,544 | 6/1979 | Louderback . |
| 4,327,076 | 4/1982 | Puglia et al. . |
| 4,327,077 | 4/1982 | Puglia et al. . |
| 4,371,557 | 2/1983 | Oppy et al. . |
| 4,588,744 | 5/1986 | McHugh . |
| 4,701,417 | 10/1987 | Portenhauser et al. . |
| 4,865,871 | 9/1989 | Livesey et al. . |
| 4,883,762 | 11/1989 | Hoskins . |
| 4,891,319 | 1/1990 | Roser . |
| 5,098,893 | 3/1992 | Franks et al. . |
| 5,290,765 | 3/1994 | Wettlaufer et al. . |
| 5,348,852 | 9/1994 | Bonderman . |
| 5,422,384 | 6/1995 | Samuels et al. . |
| 5,955,448 | * 9/1999 | Colaco et al. ........................ 519/53 |

FOREIGN PATENT DOCUMENTS

| | | |
|---|---|---|
| 0090356 | 10/1983 | (EP) . |
| 0222313 | 5/1987 | (EP) . |
| 0415567 | 3/1991 | (EP) . |
| 0430045 A2 * | 6/1991 | (EP) . |
| 0600730 | 6/1994 | (EP) . |
| 2206273 | 1/1989 | (GB) . |
| WO 87/00196 | 1/1987 | (WO) . |
| WO 89/06542 | 7/1989 | (WO) . |
| WO 91/18091 | 11/1991 | (WO) . |
| WO 92/02133 | 2/1992 | (WO) . |
| WO 95/33488 | 12/1995 | (WO) . |

OTHER PUBLICATIONS

Ablett, S., et al. (1992) "Differential scanning calorimetric study of frozen sucrose and glycerol solutions" *J. Chem. Soc. Faraday Trans.* 88:789–794.

Akers, M.J., et al. (1994) Top 10 current technical issues in parenteral science: *Pharm. Tech.* 18:26, 28, 30–33, 36.

Blakeley, D., et al. (1990) "Dry instant blood typing plate for bedside use" *The Lancet* 336:854–855.

Burke, M.J. (1985) "The glassy state and survival of anhydrous biological systems" *Membranes, Metabolism and Dry Organisms* Leopold, ed., Cornell Univ. Press, Ithaca, New York, Appendix D, pp. 358–363.

Carpenter, J.F., et al. (1988) "The mechanism of cryoprotection of proteins by solutes" *Cryobiology* 25:244–255.

Carpenter, J.F., et al. (1988) "Modes of stabilization of a protein by organic solutes during desiccation" *Cryobiology* 25:459–470.

Clegg, J.S. (1985) "The physical properties and metabolic status of Artemia cysts at low water contents: The 'water replacement hypothesis'" *Membranes, Metabolism and Dry Organisms* Leopold, ed., Cornell Univ. Press, Ithaca, New York, Chapter 10, pp. 169–187.

Colaco, C., et al. (1992) "Trehalose stabilisation of biological molecules" *Biotechnol. Intl.* Century Press, London, pp. 345, 347–350.

Colaco, C., et al. (1992) "Extraordinary stability of enzymes dried in trehalose: Simplified molecular biology" *Bio/Technol.* 10:1007–1011.

Crowe, J.H., et al. (1990) "Are freezing and dehydration similar stress vectors? A comparison of modes of interaction of stabilizing solutes with biomolecules" *Cryobiology* 27:219–231.

Crowe, J.H., et al. (1993) "Preserving dry biomaterials: The water replacement hypothesis, part I" *BioPharm* 6:28–29, 32–33, 37.

(List continued on next page.)

Primary Examiner—Gary Geist
Assistant Examiner—Leigh C. Maier
(74) Attorney, Agent, or Firm—Saliwanchik, Lloyd & Saliwanchik

(57) ABSTRACT

The present invention encompasses methods of increasing stability of biological substances during drying and the dried compositions derived therefrom. The compositions have improved storage stability.

16 Claims, 7 Drawing Sheets

OTHER PUBLICATIONS

Dialog™ Abstract of European Patent Application No. 0433679 (Jun. 26, 1994).

Finot, P.A., et al. eds., (1990) *The Maillard Reaction in Food Processing, Human Nutrition and Physiology*, Birkhäuser Verlag, Basel.

Franks, F., (1990) "Freeze drying: From empiricism to predictability" *Cryo–Letters* 11:93–110.

Franks, F., et al.(1991) "Materials science and the production of shelf–stable biologicals" *BioPharm* 14:38, 40–42, 55.

Franks, F., et al. (1993) "Stable enzymes by water removal" *Stability and Stabilization of Enzymes* van den Tweel, W.J.J., et al., eds., Elsevier, Amsterdam, pp. 45–54.

Franks, F. (1994) "Long–term stabilization of biologicals" *Bio/Tech*. 12:253–256.

Green, J.L., et al. (1989) "Phase relations and vitrification in saccharide–water solutions and the trehalose anomaly" *J. Phys. Chem.* 93:2880–2882.

Harrington, C.R., et al. (1994) "A glycation connection" *Nature* 370:247–248.

Ledl, F., et al. (1990) "New aspects of the Maillard reaction in foods and in the human body" *Ang. Chem.* 29:565–595.

Levine, H., et al. (1992) "Another view of trehalose for drying and stabilizing biological materials" *BioPharm* 5:36–40.

Nursten H.E. (1986) "Maillard browning reactions in dried foods" *Concentrating and Drying of Foods* McCarthy, D., ed., Elsevier Applied Science, London, pp. 53–68.

Pikal et al. (1990) "Freeze–drying of proteins. Part 1: Process design " *BioPharm* 3:18–20, 22–23, 26–27.

Reynolds, T.M. (1965) "Chemistry of nonenzymic browning II" *Adv. Food Res.* 14:167–283.

Roos, Y., (1993) "Melting and glass transitions of low molecular weight carbohydrates" *Carbohydrate Res.* 238:39–48.

Roser, B., (1991) "Trehalose drying: A novel replacement for freeze drying" *BioPharm* 4:47–53.

Roser, B., et al. (1993) "A sweeter way to fresher food" *New Scientist* 138:25–28.

Slade, L., et al. (1988) "Non–equilibrium behavior of small carbohydrate–water systems" *Pure & Appl. Chem.* 60:1841–1864.

Smith, M. A., et al. (1994) "Advanced Maillard reaction end products are associated with Alzheimer disease pathology" *Proc. Natl. Acad. Sci. USA* 91:5710–5714.

Vitek, M.P., et al. (1994) "Advanced glycation end products contribute to amyloidosis in Alzheimer disease" *Proc. Natl. Acad. Sci. USA* 91:4766–4770.

Written Opinion from the International Preliminary Examining Authority (PCT) dated May 13, 1996 directed to the International Application No. PCT/GB95/01967.

\* cited by examiner

METHOD FOR STABILIZATION OF BIOLOGICAL SUBSTANCES DURING DRYING AND SUBSEQUENT STORAGE AND COMPOSITIONS THEREOF

CROSS-REFERENCE TO RELATED APPLICATIONS

This application is a continuation of prior U.S. application Ser. No. 08/293,157, now U.S. Pat. No. 5,955,448 filed Aug. 19, 1999.

STATEMENT OF RIGHTS TO INVENTIONS MADE UNDER FEDERALLY SPONSORED RESEARCH

Not applicable

BACKGROUND ART

The present invention relates generally to methods for increasing stabilization of biological substances during drying, and storage of dry formulations. Compositions of stabilized biological substances are also provided. Storage stability is the ultimate goal for dried formulations of biological substances. Dried formulations are preferred to aqueous formulations as the water, a nucleophile in hydrolysis reactions and a plasticizer, increases the molecular mobility of reactive chemical species, making aqueous formulations of biological substances inherently less stable than their dry counterparts. This increased stability of dry formulations has focused attention on techniques of drying and led to the development of freeze-drying as a popular method of water removal. Pikal (1990a) *Biopharm.* 3:18–27; Pikal (1990b) *Biopharm.* 3:26–30; and Franks (1990) *Cryoletters*11:93–100. However, despite its widespread use, many freeze-dried products are still unstable at ambient temperatures. Carpenter and Crowe (1988) *Cryobil.* 25:244–255; and Crowe et al. (1990) *Cryobil.* 27:219–231. Detailed theoretical analyses of the physicochemical events during freeze-drying have led to a substantial literature on the use of lyoprotectants as stabilizing excipients. Pikal (1990b); Carpenter and Crowe (1988); Crowe et al. (1990); and Levine and Slade (1988) *Pure Appl. Chem.* 60:1841–1864. Various carbohydrates have been advocated as stabilizing excipients in freeze-drying, and these are proposed to act via the generation of an amorphous, glassy, solid state in the freezing step. Pikal (1990b); Franks (1990); Levine and Slade (1988); and Franks et al. (1992) U.S. Pat. No. 5,098,893. Nevertheless, the freezing step remains a major variable, as evidenced by the equivocal values for the experimentally measured glass transition temperature of the maximally freeze-concentrated unfrozen matrix (T'g) for various carbohydrate excipients. Franks (1990); Levine and Slade (1988); Ablett et al. (1992) *J. Chem. Soc. Faraday Trans.* 88:789–794; and Roos (1993) *Carbo. Res.* 238:39–48.

Exposure to temperatures above the glass transition or collapse during freeze drying can result in significant activity losses. Furthermore, freezing is thought to be the major cause of protein damage during freeze-drying. Due to the loss of activity on freeze drying, recent attention has focused on the techniques of ambient temperature drying. These not only eliminate the freezing step but are more rapid and energy-efficient in the removal of water during drying. Crowe et al. (1990); Roser (1991) *Biopharm.* 4:47–53; Roser and Colaco (1993) *New Scientist* 138:24–28; Blakely et al. (1990) *The Lancet* 336:854–55; Colaco et al. (1990) *Biotech. Intl.* pp. 345–350, Century Press, London; Colaco et al. (1992) *Biotech.* 10:1007–1011; Franks (1991) *Biopharm.* 14:38–55; Franks and Hatley (1993) in "*Stability and stabilization of enzymes*", eds. van den Tweel et al., Elsevier, Amsterdam (1993) pp. 45–54; and Franks (1994) *Bio/Tech.* 12:253–256; Roser, U.S. Pat. No. 4,891,319; and Roser et al. (1991) WO91/18091.

All references cited herein, both supra and infra, are hereby incorporated herein by reference.

Stabilization of dried biological substances, particularly at ambient or higher temperatures, remains a challenge. One carbohydrate, trehalose ($\alpha$-D-glucopyranosyl-$\alpha$-D-glucopyranoside), has been found to be uniquely potent in prolonging shelf life of dried proteins and other biological materials for prolonged periods at ambient or higher temperatures. Stability has been assessed by recovery of biological activity upon rehydration. Roser (1991); Roser and Colaco (1993); Blakely et al. (1990); Colaco et al. (1990); Colaco et al. (1992); and Carpenter and Crowe (1988) *Cryobil.* 25:459–470. Studies of other sugars, polyhydric alcohols and oligosaccharides under conditions identical to those in which trehalose provides protein stability, showed that this degree of stabilization is unique to trehalose. Some of these excipients are partially protective, however, in that they protect the biomolecules from damage during the drying process itself and confer more limited tolerance to high temperatures. Crowe et al. (1990); Roser (1991); Colaco et al. (1990); Crowe et al. (1987); Carpenter et al. (1987); and Carpenter and Crowe (1988).

There are two main hypotheses that have been postulated with respect to the molecular mechanism by which trehalose stabilizes biological molecules. Clegg (1985) in *Membranes, metabolism and dry organisms*, ed. Leopold, Cornell Univ. Press, Ithaca, N.Y., pp. 169–187; Burke (1985) in *Membranes, metabolism and dry organisms* ed. Leopold, Cornell Univ. Press, Ithaca, N.Y., pp. 358–363; Green and Angell (1989) *J. Phys. Chem.* 93:2280–2882; Levine and Slade (1992) *Biopharm.* 5:36–40; and Crowe et al. (1990) *Biopharm.* 6:28–37. The water replacement theory states that, being a polyol, trehalose can make multiple external hydrogen bonds which could replace the essential structural water molecules that are hydrogen-bonded to biomolecules and thus maintain their molecular structure. Clegg (1985); and Crowe et al. (1993). The glassy state theory postulates that, as the drying trehalose solutions undergo glass transformation, this results in an amorphous continuous phase in which molecular motion, and thus degradative molecular reactions, are kinetically insignificant. Burke (1985); Green and Angell (1989); and Levine and Slade (1992). Results previously obtained and those described herein are not consistent with either hypothesis being a sufficient sole explanation for the mechanism of action of trehalose.

The water replacement theory suggests that, as polyols, sugars other than trehalose should also be effective as stabilizing excipients, and, if the specific spatial combinations of hydroxyl groups are the crucial feature, then glucose should be as effective as trehalose. However, results obtained previously and presented herein show that glucose, a polyol, is among the least effective of a variety of sugars tested (see Table 1), and none of the other polyols tested was found to be as effective as trehalose (FIG. 1 and Table 1). Furthermore, if molecular mimicry of water was important, as might be expected for water replacement, then scylloinositol (with all its hydroxyl groups being axial) should, in theory, be the most effective carbohydrate, but it is among the least effective in practice. Thus, the water replacement theory cannot be a complete explanation for the mechanism of action of trehalose. Similarly, the glassy state theory alone cannot explain the stability conferred by trehalose. In high temperature storage stability data reported in FIG. 1 above, the glass transition temperatures of the samples dried in trehalose to a water content of 2.6–3.6% were all below 37° C. as measured by differential scanning calorimetry. Thus, their stability persists at well above their glass transition temperatures, and although the glassy state may be important in other systems, contrary to accepted belief (Franks et al. (1992); and Franks (1994)), it appears not to be a factor in the long-term high temperature stability of biomolecules dried in trehalose.

Although current belief is that protein stability depends almost solely on glass transition temperature, several possible contributing reactions that decrease protein stability in the presence of sugars have been proposed. Franks (1994). These possible reactions have not been analyzed and are thought to contribute little, if any, to protein instability. Franks et al. (1994); and Akers and Nail (1994) *Pharm. Tech.* 18:26–36.

DISCLOSURE OF THE INVENTION

The present invention encompasses methods of increasing stability of biological substances during drying and the dried compositions derived therefrom. One method includes drying the biological substances in the presence of a carbohydrate excipient in an amount effective to stabilize the dried biological substance and an inhibitor of the Maillard reaction in an amount effective to substantially prevent condensation of amino groups and reactive carbonyl groups.

Another method includes increasing storage stability of dried biological substances by storing the substances in the presence of a carbohydrate excipient in an amount sufficient to stabilize the biological substance and an inhibitor of the Maillard reaction in an amount sufficient to substantially prevent condensation of amino groups and reactive carbonyl groups. Compositions of biological substances, carbohydrates and inhibitors of the Maillard reaction are also included.

BEST MODE FOR CARRYING OUT THE INVENTION

Figure 1:
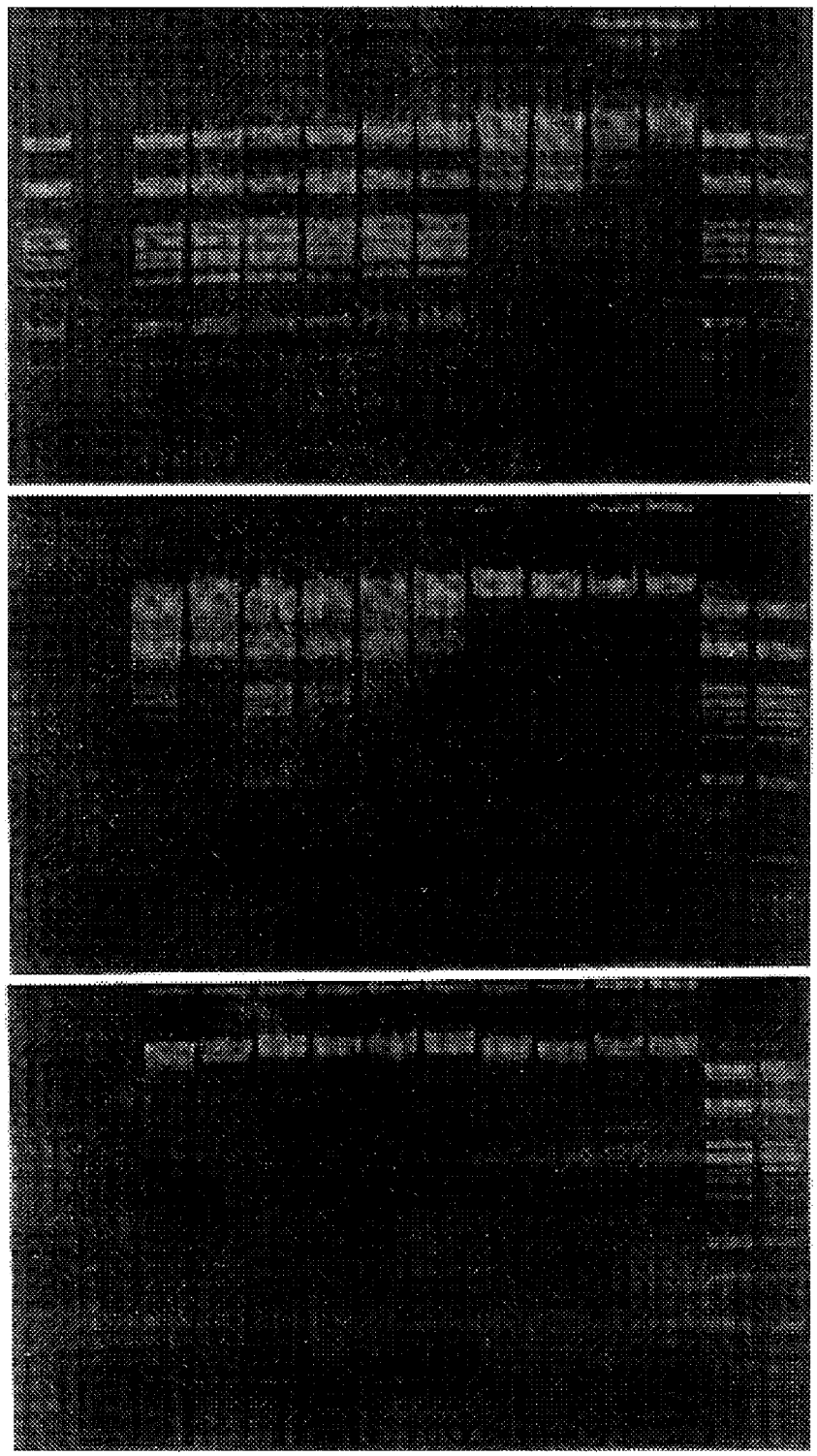
FIG. 1. Accelerated aging study on the restriction enzyme Pst I.

Previous work of the stabilization of dry protein formulations in the presence of carbohydrate excipients has emphasized the ability of stabilizing excipients to replace structural water and/or provide an amorphous or glassy solid matrix in the dry state. These studies have failed to realize the effect and nature of chemical reactions during drying and storage subsequent to drying. As shown in the examples presented herein, these reactions, which may begin during drying, are greatly enhanced during storage. These examples show that the Maillard reaction is the main chemical reaction occurring during drying and upon storage of dried biological substances in the presence of carbohydrate excipients. The methods and formulations described herein prevent the Maillard reaction during storage and thus increase shelf life of stored, dried biological substances.

The Maillard reaction is actually a cascade of chemical reactions initiated by the reversible spontaneous condensation of reactive carbonyl and amino groups to form a Schiffs base. The activation energy of the initial condensation to form the Schiff's base is only on the order of 10–15 kcal, is reversible in the presence of water, and the equilibrium is largely in favor of the reactants in aqueous environments. Reynolds (1965) *Adv. Food Res.* 14:167–283; Finot et al. (1990) *The Maillard Reaction in Food Processing, Human Nutrition and Physiology* Birkhauser, Basel; and Lendl and Schleicher (1990) *Ang. Chem.* 29:565–594. A schematic of the components of the Maillard reaction is presented in FIG. 3. Formation of the Schiffs base is a cascade of subsequent reaction resulting in the cross-linking of the proteins involyed and the generation of brown melanoid pigments. The subsequent spontaneous Amadori or Heyns rearrangement of the Schiffs base is irreversible and triggers a complex series of reactions that ultimately result in the production of brown melanoidin pigments and both fragmentation and cross-linking of the proteins involved. In the food industry, the Maillard reaction has been widely studied, as it is one of several causes of spoilage, especially of dried food products, during storage. It has even been observed during refrigerated storage of foodstuffs with high protein and sugar contents. The Maillard reaction is a particular problem with dry foodstuffs, as the equilibrium of the reaction is forced towards the formation of the Schiffs base by the loss of water, and many of the subsequent reactions are accelerated at low water activities. Lendl and Schleicher (1990); and Nursten (1986) in *Maillard browning reactions in dried foods in concentration and drying of foodstuffs*, ed. McCarthy Elsevier Applied Science, London.

The present invention encompasses methods of increasing stability of biological substances during drying and storage and dried compositions thereof with increased storage stability. In the methods and compositions, although singular forms may be used, more than one carbohydrate, more than one biological substance and more than one inhibitor of the Maillard reaction may be present. Determination of the effective amounts of these compounds is within the skill of one in the art.

The biological substances may be derived from natural sources or chemically synthesized. Typically they are biologically active, or are able to exert a biological effect. However, intermediates or combinations of active compounds and intermediates are also encompassed. Likewise, formulations of carbohydrates and inhibitors of the Maillard reaction into which biological substances are to be incorporated are encompassed by the present invention. The biological substances may be any known in the art and include, but are not limited to, subcellular compositions, cells, viruses and molecules including, but not limited to, those containing free amino, imino and guanidino side chains, although singular forms may be used. Such molecules include, but are not limited to, pharmaceutical agents, lipids, organics, peptides, proteins, hormones (peptide, steroid and corticosteroid), oligosaccharides, synthetic peptides, D and L amino acid polymers, nucleic acids, protein nucleic acid hybrids and small molecules. Suitable proteins include, but are not limited to, enzymes, biopharmaceuticals, growth hormones, growth factors, monoclonal antibodies, and cytokines. Organics include, but are not limited to, pharmaceutically active chemicals with amino, imino or guanidino groups.

The method of drying may be any known in the art and includes, but is not limited to, freeze drying, spray drying, fluidized-bed drying, drum drying, drying at ambient temperature and atmospheric pressure, drying at ambient temperature and decreased pressure, drying at elevated temperatures and atmospheric pressure and drying at elevated temperatures and decreased pressure. In the case of freeze drying, the samples are typically frozen at −70 to −30° C. and dried at a condenser temperature of −50 to −80° C., although any suitable temperature may be used. Freezing can be performed by any method known in the art including, but not limited to, immersing in liquid nitrogen, placing in a freezer which may be at −4° C. to −80° C. and a dry ice and alcohol freezing bath. In the case of ambient or elevated temperature drying, any temperature above freezing may be used, provided it is not so high that the biological substance becomes denatured; preferably the temperatures are less than 80° C., more preferably less than 65° C. and most preferably 20–50° C. Preferably the temperature is above ambient to 50° C. In the case of spray drying, the temperature range is less than 250° C., more preferably in the range of 150–220° C., and most preferably, 180–200° C.

As used herein, with respect to storage or drying, ambient, or "room temperature" is generally about 20° C. and elevated temperatures are all those above freezing. Temperatures "above ambient" are those greater than 20° C.

As used herein, the term "carbohydrates" includes, but is not limited to, disaccharides, trisaccharides, oligosaccharides and their corresponding sugar alcohols, polyhydroxy compounds, such as carbohydrate derivatives and chemically modified carbohydrates, hydroxyethyl starch and sugar copolymers (Ficoll). Both D and L forms of the carbohydrates may be used. When the biological substance is used in a pharmaceutical preparation, the carbohydrate selected is physiologically acceptable. The carbohydrate may be non-reducing or reducing. As described in the examples presented herein, it has now been found that, surprisingly, non-reducing carbohydrates can hydrolyze to form reducing carbohydrates upon storage in dried compositions and initiate the formation of Schiffs bases with the substances stored therein. This condensation results in the formation of water which plasticizes the system, resulting in increased mobility of the chemical entities, thus enhancing the rate of the degradative reactions, including the Maillard reaction. Thus, the present invention is particularly useful with non-reducing carbohydrates.

Reducing carbohydrates suitable for use in the present invention are those known in the art and include, but are not limited to, glucose, maltose, lactose, maltulose, iso-maltulose and lactulose.

Non-reducing carbohydrates include, but are not limited to, non-reducing glycosides of polyhydroxy compounds selected from sugar alcohols and other straight chain polyalcohols. Other useful carbohydrates include raffinose, stachyose, melezitose, dextran and sugar alcohols. The sugar alcohol glycosides are preferably monoglycosides, in particular the compounds obtained by reduction of disaccharides such as lactose, maltose, lactulose and maltulose. The glycosidic group is preferably a glucoside or a galactoside and the sugar alcohol is preferably sorbitol (glucitol). Particularly preferred carbohydrates are maltitol (4-O-β-D-glucopyranosyl-D-glucitol), lactitol (4-O-β-D-galactopyranosyl-D-glucitol), iso-maltulose, palatinit and its constituent isomers (GPS, α-D-glucopyranosyl-1→6-sorbitol and GPM, α-D-glucopyranosyl-1→6-mannitol), the sugar alcohol derived from isomaltulose (palatinose) (6-α-D-glucopyranosyl-mannitol and 6-α-D-glucopyranosyl-sorbitol), sucrose and their sugar alcohols.

The inhibitor of the Maillard reaction can be any known in the art. When the biological substance is used in a pharmaceutical preparation, the inhibitor selected is physiologically acceptable. The inhibitor is present in an amount sufficient to prevent, or substantially prevent, condensation of amino groups and reactive carbonyl groups. Typically, the amino groups are present on the biological substance and the carbonyl groups are present on the carbohydrate. However, the amino and carbonyl groups may be intramolecular within either the biological substance or the carbohydrate. Various classes of compounds are known to exhibit an inhibiting effect on the Maillard reaction and hence to be of use in the compositions described herein. These compounds are generally either competitive or noncompetitive inhibitors. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known noncompetitive inhibitors. These include, but are not limited to, aminoguanidine derivatives, amphotericin B and the following. EP-A-0 433 679 describes 4-hydroxy-5,8-dioxoquinoline derivatives of the following formulae.

(a) a 4-hydroxy-5,8-dioxoquinoline derivative of the formula (I) or a salt thereof:

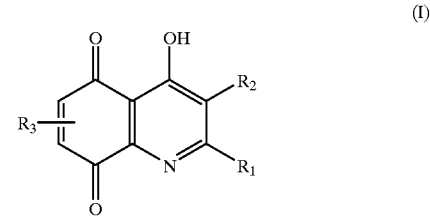

wherein $R_1$ and $R_2$ are each hydrogen, methyl, trifluoromethyl, carboxy, methoxycarbonyl or ethoxycarbonyl, and $R_3$ is hydrogen or hydroxy;

(b) a 4,5,8-trihydroxyquinoline derivative of the formula (II) or a salt thereof:

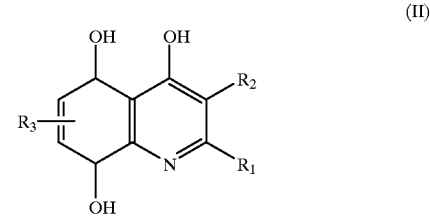

wherein $R_1$, $R_2$ and $R_3$ are as defined herein;

(c) a 3-oxophenoxazine derivative of the formula (III) or a salt thereof:

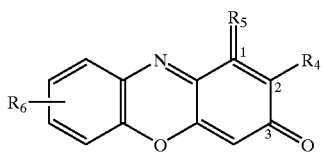

(III)

wherein R4 and R5 are each hydrogen or form by incorporation of $C_1$ and $C_2$ carbon atoms a condensed [2,1-b] pyridine ring optionally substituted with a hydroxyl group and/or a carboxyl group, and R6 is hydrogen or hydroxy; or (d) a 3-oxophenoxazine N-oxide of the formula (IV) or a salt thereof:

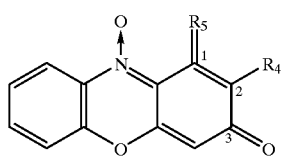

(IV)

wherein $R_4$, $R_5$ and $R_6$ are as defined hereine

EP-A-O 430 045 similarly discloses ascorbic acid tocopheryl phosphate diesters having Maillard reaction-inhibiting action, namely compounds of the formula:

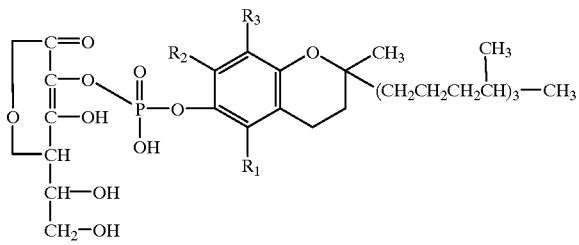

(V)

wherein $R_1$, $R_2$ and $R_3$ independently of one ano ther denote hydrogen or methyl, or a salt thereof.

Also EP-A-O 325 936 describes aminoguanidine derivatives of the general formula:

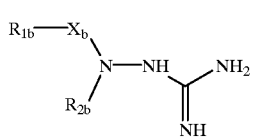

(VI)

(wherein $R^{1b}$ represents carbocyclic or heterocyclic ring substituted or unsubstituted by from 1 to 3 group(s) selected from halogen atom, alkyl or alkoxy group of from 1 to 4 carbon atom(s), nitro group, phenoxy group, amino group, hydroxy group and acylamino a group of from 2 to 4 carbon atom(s), $X_b$ represents single-bond, alkylene group of from 1 to 4 carbon atom(s) or alkenylene group of from 2 to 4 carbon atoms, or $R^{1b}$ together with $X_b$ represents alkyl group of from 1 to 4 carbon atom(s), $R^{2b}$ represents hydrogen atom, alkyl group of from 1 to 4 carbon atom(s) or phenyl group substituted or unsubstituted by from 1 to 3 group(s) selected from halogen atom, alkyl or alkoxy group of from 1 to 14 carbon atom(s), hydroxy and nitro group, or an acid addition salt thereof.

In one preferred embodiment, the method of drying is freeze drying and the Maillard inhibitor is a competitive inhibitor. In another preferred embodiment, the method of drying is freeze drying and the Maillard inhibitor is a noncompetitive inhibitor. In another preferred embodiment, the method of drying is at ambient or elevated temperatures and the Maillard inhibitor is a competitive inhibitor. In another preferred embodiment, the method of drying is at ambient or elevated temperatures and the Maillard inhibitor is a noncompetitive inhibitor.

The invention also encompasses methods of increasing the "shelf-life" or storage stability of dried biological substances stored at elevated temperatures. Increased storage stability is determined by recovery of biological activity in accelerated aging trials. The methods include drying, or otherwise incorporating, at least one biological substance in the presence of at least one carbohydrate excipient in an amount sufficient to stabilize the biological substance, and at least one inhibitor of the Maillard reaction. Other suitable buffers, salts, cofactors, etc., may be added to the composition. The composition may be stored at any suitable temperature. Preferably, the compositions are stored at 0° C. to 80° C. More preferably, the compositions are stored at 20° C.–60° C. Most preferably, the compositions are stored at above ambient temperatures.

The invention also encompasses compositions with increased storage stability comprising a biological substance, a carbohydrate in an amount sufficient to stabilize the dried biological substance and an inhibitor of the Maillard reaction wherein the carbohydrate is present in an amount sufficient to stabilize the biological substances upon drying and the inhibitor is present in an amount sufficient to substantially prevent condensation of amino groups on the biological substances and reactive carbonyl groups therein, or on the carbohydrate stabilizing excipient, or generated therefrom. Preferably, the compositions have increased storage stability at 0° C.–250° C. More preferably, the compositions have increased storage stability at 20° C.–50° C. Most preferably, the compositions have increased stability at above ambient temperatures.

Preferably, the composition is almost completely dry so as to increase stability of the molecule by decreasing the Maillard reaction during storage. Some water or other aqueous solvent may remain in the composition but preferably, not more than 20%. As used herein, "dry," "dried," and "substantially dried" encompass those compositions with from about 0–20% water. Preferably, less than about 20% water is present, more preferably less than about 10% water is present, and most preferably less than about 5% water is present.

The compositions may be obtained by any of the methods described above and may contain any of the components described above. Although actual weights and percentages of the various components of the compositions are not given, they are within the skill of one in the art to determine without undue experimentation given the disclosure herein.

EXAMPLES

Example 1

Trehalose Stabilization of Biomolecules

It has previously been shown that antibodies, air-dried in the presence of trehalose, are undamaged, and full biological activity is recovered on rehydration, even after several years storage at room temperature or 37° C. Roser (1991); Blakely et al. (1990); and Colaco et al. (1990). Similar results were obtained with a variety of enzymes, hormones and blood coagulation factors, suggesting that this process may be generally applicable to biological substances. Roser (1991); Roser and Colaco (1993); Blakely et al. (1990); Colaco et al. (1990); and Colaco et al. (1992). As a stringent test of this technology to preserve labile biological substances, the enzymes used in molecular biology, which are notoriously fragile and thus usually transported and stored at or below −20° C., were studied in detail. It has previously been shown that both restriction endonucleases and DNA modifying enzymes can be dried from trehalose solutions at ambient temperatures without loss of activity. Furthermore, these dried enzymes show stability on storage for extended periods even at elevated temperatures. Colaco et al (1992).

In order to determine the ability of carbohydrates other than trehalose to preserve activity in proteins, an accelerated aging study was performed with the restriction enzyme PstI vacuum-dried with supplemental heating to a residual moisture content of 2.6–3.6% in a number of carbohydrate excipients and stored for one month at either 37° C., 55° C. or 70° C.

The results obtained are presented in Table 1 and FIG. 1. Five units of fresh enzyme control (track 1) was compared, for the ability to cut bacteriophage λ DNA, with 2.5 unit (FIG. 1. even numbered tracks) or 5 unit (FIG. 1, odd numbered tracks) of enzyme dried using various carbohydrate excipients and stored for 35 days at 37° C. (FIG. 1, top panel), 55° C. (FIG. 1, middle panel) and 70° C. (FIG. 1, bottom panel). The carbohydrate excipients were used Glucopyranosyl-mannitol (FIG. 1, tracks 3 & 4) or sorbitol (FIG. 1, tracks 5 & 6), reduced isomaltose (FIG. 1, tracks 7 & 8), sucrose (FIG. 1, tracks 9 & 10), maltose (FIG. 1, tracks 11 & 12) and trehalose (FIG. 1, tracks 13 & 14). As can be seen from FIG. 1, only trehalose shows any stabilizing effects at the two higher temperatures studied.

Although some of the carbohydrate excipients stabilized the enzyme during drying and on storage at 37° C. (FIG. 1, top panel, Table 1), only the samples stabilized using trehalose retained activity when stored at either 55° C. or 70° C. (FIG. 1, middle and bottom panels, Table 1). These results have now been correlated with real-time data and emphasize the finding that, with respect to long-term stability, trehalose is a better stabilizing excipient than the other carbohydrates tested under identical drying and storage conditions (Table 1). All the monosaccharides were ineffective, whether reducing or non-reducing, as were polymers such as inulin, ficoll and dextran (Table 1). Reducing sugars, such as lactose and maltose, failed within a month at the lowest temperature studied, 37° C., as did the non-reducing disaccharide sucrose (Table 1). The chemically more stable non-reducing sugars, the sugar alcohols, showed better stabilities than their reducing counterparts, but still failed within a month at 55° C. (Table 1).

TABLE 1

STABILITY OF PST I DRIED IN VARIOUS CARBOHY

| CARBOHYDRATE | CHEMICAL NAME | SUGAR |
|---|---|---|
| MONOSACCHARIDES AND ALCOHOLS | | |
| Glucose | α-D-glucopyranose | + |
| Sorbitol | sugar alcohol of glucose | − |
| Galactose | α-D-galactopyranose | + |
| Galactitol | sugar alcohol of galactose | − |

TABLE 1-continued

STABILITY OF PST I DRIED IN VARIOUS CARBOHY

| CARBOHYDRATE | CHEMICAL NAME | SUGAR |
|---|---|---|
| Mannose | α-D-mannopyranose | + |
| Mannitol | sugar alcohol of mannose | − |
| DISACCHARIDES | | |
| Trehalose | α-D-glucopyranosyl-α-D-glucopyranoside | − |
| Maltose | 4-O-α-D-glucopyranosyl-D-glucose | + |
| Maltotriose | O-α-D-glucopyranosyl(1→4)-O-α-D-glucopyranosyl-(1→4)-D-glucose | + |
| Lactose | 4-O-β-D-galactopyranosyl-D-glucopyranose | + |
| Lactulose | 4-O-β-D-galactopyranosyl-D-fructose | + |
| Sucrose | β-D-fructofuranosyl-α-D-glucopyranoside | − |
| POLYMERS | | |
| Inulin | Polymer of 1-O-β-D-fructofuranosyl-D-fructose | − |
| Dextran | Polymer of α-(1→6)-D-glucopyranose (1→3, 1→4 branch) | + |
| Ficoll | Polymer of β-D-fructofuranosyl-α-D-glucopyranose | − |

Quantitation of activity | Reducing properties

− no detectable activity  + reducing sugar
+ some activity (10–20% of titre)  − non-reducing sugar
++ partial activity (25–40% of titre)
+++ full activity Example 2

Non-Enzymatic Browning of Dried Formulations During Storage

Figure 2:
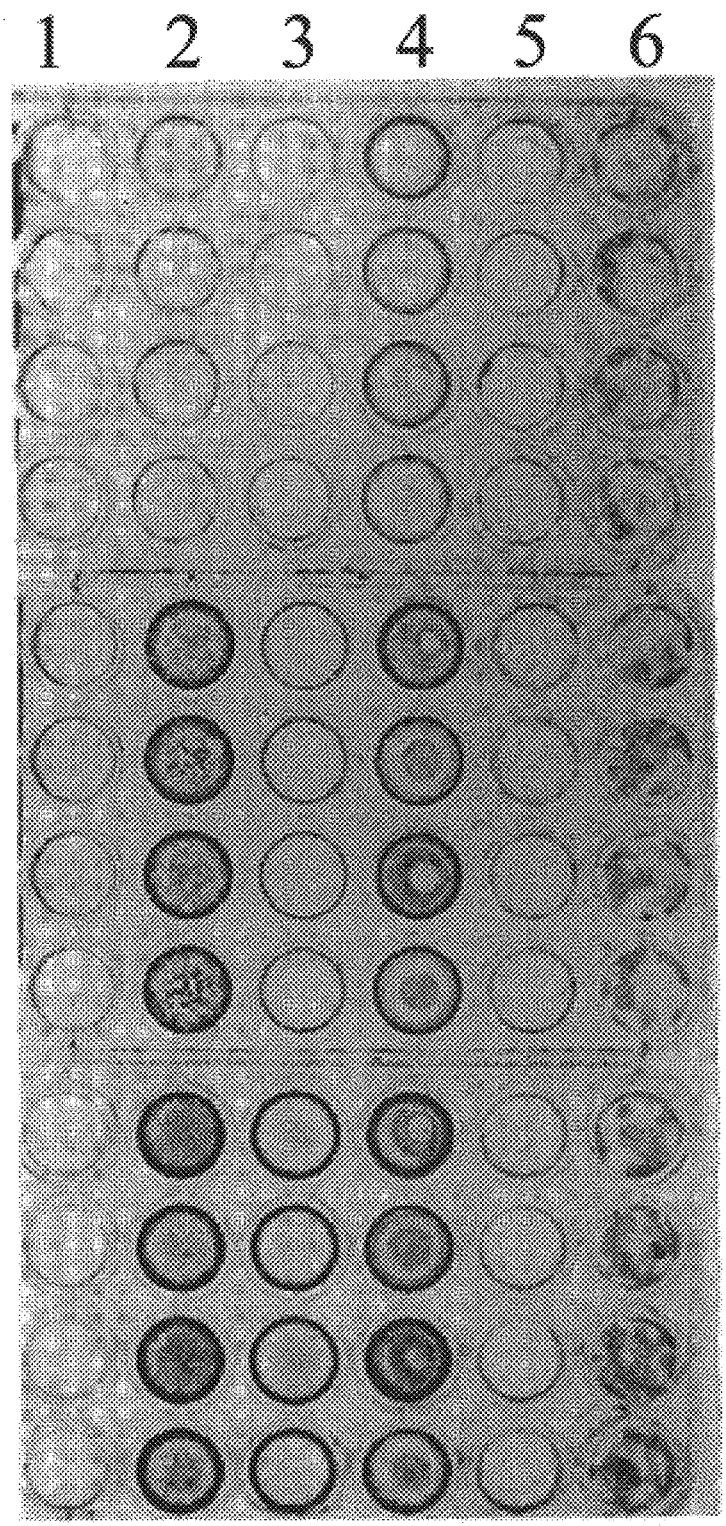
FIG. 2. Non-enzymatic browning of the samples studied for accelerated aging.

It appears that the relative chemical stability and non-reducing nature of trehalose may be significant features in its mechanism of action, especially with regard to the long term stability observed at high temperatures. This was first suggested by a surprising feature observed in the accelerated ageing trial described in FIG. 1 above. As shown in FIG. 2, non-enzymatic browning was observed in the samples used in the accelerated ageing study reported in FIG. 1 after two weeks storage at 37° C. (top panel), 55° C. (middle panel) and 70° C. (bottom panel). The carbohydrate excipients used were trehalose (row 1), sucrose (row 2), maltose (row 3), reduced iso-maltulose (row 4), glucopyranosyl-sorbitol (row 5) and glucopyranosyl-mannitol (row 6).

The results obtained indicate that the development of a brown coloration developed in a number of the sample wells at all three temperatures after just two weeks of storage of the sample. Furthermore, the extent of the coloration appeared to correlate with the reduction in enzymatic activity in these samples. Increasing coloration was observed in the samples stored at higher temperatures (FIG. 2), which also showed the greatest loss of activity (FIG. 1). This coloration was highly reminiscent of the non-enzymatic browning seen during the processing and storage of food products. This non-enzymatic browning is the result of the spontaneous reaction between the reducing sugars and proteins that are natural constituents of these foodstuffs, and has been widely studied in food chemistry under the umbrella of the so-called Maillard reaction.

Example 3

Evidence for Maillard Reactions in Dried Formulations

Studies were undertaken to correlate changes in biological activity with the development of brown pigments, as observed in the accelerated ageing studies on restriction enzymes (FIG. 2). These studies were carried out on samples of the enzyme alkaline phosphates which were dried, under the conditions described in Example 1 above, from solutions containing glucose, fructose, maltose or trehalose and stored for various periods at 55° C., before enzymatic activity was reassayed. Residual activity was determined in samples of alkaline phosphatase dried in the presence of various carbohydrate excipients and assayed calorimetrically after storage at 55° C.

Figure 3:
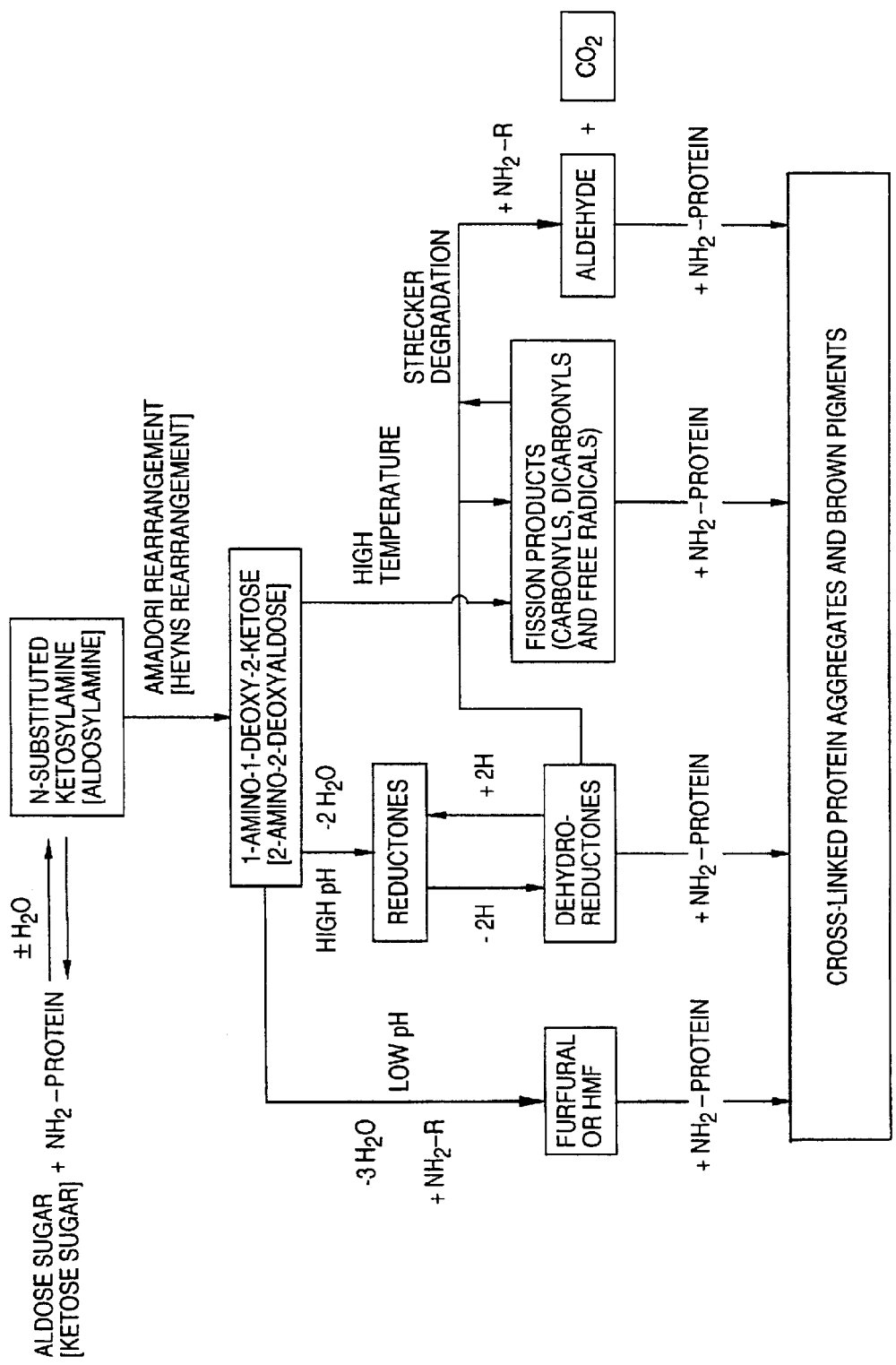
FIG. 3. Schematic of the Maillard reaction.
Figure 4:
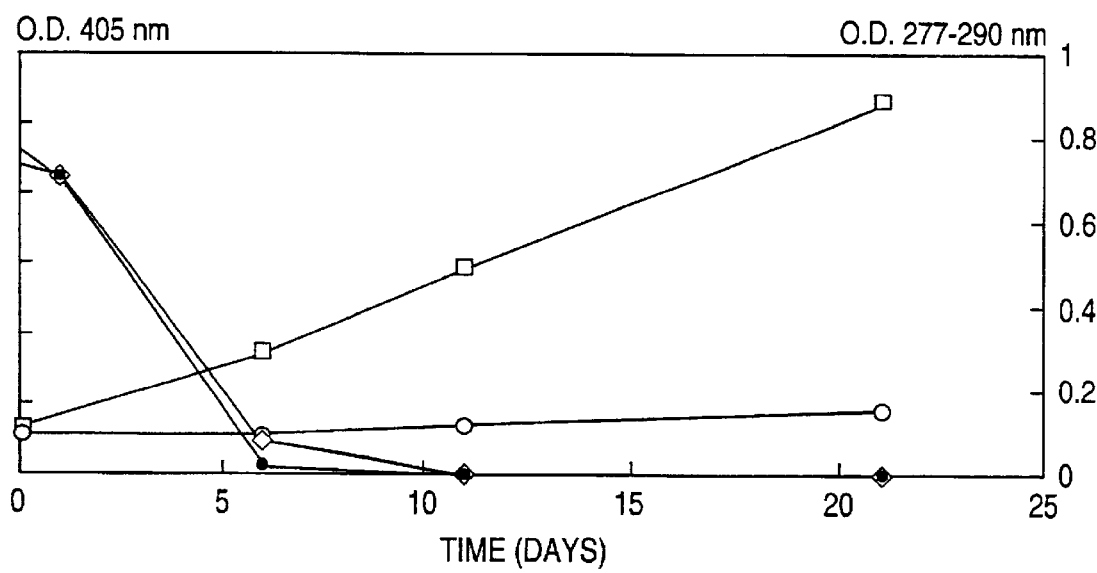
FIG. 4. Browning of alkaline phosphatase dried in the presence of fructose and glucose.

Development of brown coloration assayed by absorbance between 277–290 nm was compared with loss of enzymic activity in samples of alkaline phosphatase dried in fructose and glucose after storage at 55° C. FIG. 5 shows the results obtained where color development was measured at O.D. 277–290; (·) glucose, (+) fructose. Enzymic activity (O.D. 405); and depicted as follows: (*) glucose, (□) fructose. The production of melanoid pigments occurred later than the loss of enzymatic activity assayed calorimetrically (FIG. 4). This is consistent with the fact that the generation of brown melanoid pigments occurs in the terminal stages of the Maillard reaction and thus cannot be used to predict enzyme inactivation due to the early reactions of the cascade (FIG. 3). Similarly, analysis of the samples by SDS-PAGE showed a complex pattern of protein breakdown and cross-linking in all samples, except those dried in trehalose, and the complexity of these patterns precludes the use of this technique in determining the extent of protein modification by the Maillard reaction.

A surprising result was obtained on analysis of the residual sugar contents of the samples in the studies described above. When dried in glucose or fructose, only the individual sugars were detectable in the samples immediately post-drying. However, on loss of enzymatic activity after high temperature storage, these samples were found to contain mixtures of the two sugars. These results are presented in Table 2.

A similar isomerization was observed in the samples found to contain a mixture of glucose and maltose immediately post-drying, due to partial hydrolysis of the maltose. On loss of activity after high temperature storage, these samples were found to contain a mixture of both glucose and fructose, as well as maltose (Table 2). The absence of any mannose production detected in this non-enzymatic isomerization is indicative of chemical reaction pathway involving a common Schiffs base intermediate, similar to the formation of osazones in the Fisher reaction.

TABLE 2

HPLC ANALYSIS OF CARBOHYDRATES IN FORMULATIONS DRIED IN VARIOUS EXCIPIENTS

| CARBOHYDRATE EXCIPIENT USED IN TWO FORMULATIONS | POST DRYING ACTIVITY | POST DRYING SUGAR ANALYSIS AF |
|---|---|---|
| 1. Glucose Sample A | + | Glucose |
| 2. Glucose Sample B | + | Glucose |
| 3. Sorbitol Sample A | ++ | Sorbitol |
| 4. Sorbitol Sample B | ++ | Sorbitol |
| 5. Fructose Sample A | + | Fructose |
| 6. Fructose Sample B | + | Fructose |
| 7. Maltose Sample A | +++ | Maltose + Glucose |
| 8. Maltose Sample B | +++ | Maltose |
| 9. Sucrose Sample A | +++++ | Sucrose |
| 10. Sucrose Sample B | +++++ | Sucrose |
| 11. Trehalose Sample A | +++++ | Trehalose |
| 12. Trehalose Sample B | +++++ | Trehalose |

Example 4

Maillard-Related Modifications of Glucagon

To exemplify the generality of these chemical modifications of proteins by carbohydrate excipients, a relevant pharmaceutical model system was studied. The protein modifications of a therapeutic peptide, glucagon, dried from solution for 18 hr under a vacuum of 30 milliTorr, with a shelf-temperature rising from 25 to 42° C., were studied. Formulations containing various carbohydrate excipients were analyzed by reverse-phase HPLC analysis. The results obtained from a comparison of glucose and sucrose stored for varying times are presented in FIG. 5.

Figure 5A:
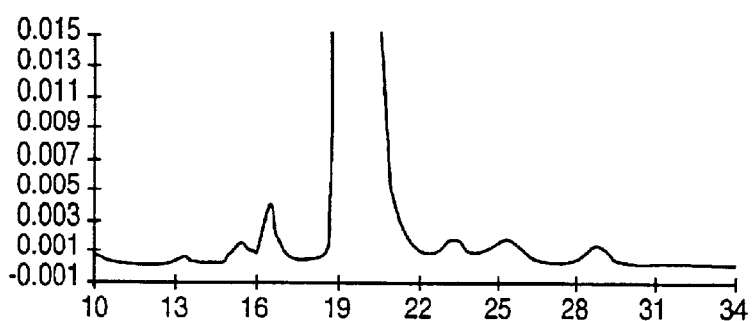
FIG. 5. HPLC analysis of glucagon dried in the presence of glucose or trehalose.
Figure 5B:
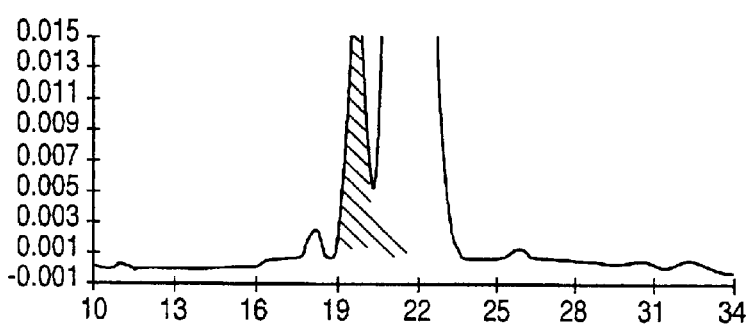
Figure 5C:
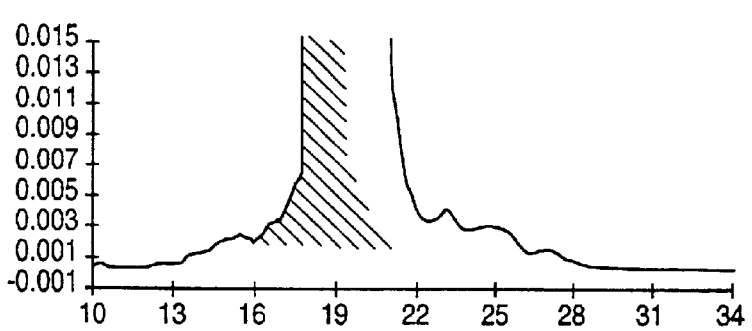
Figure 5D:
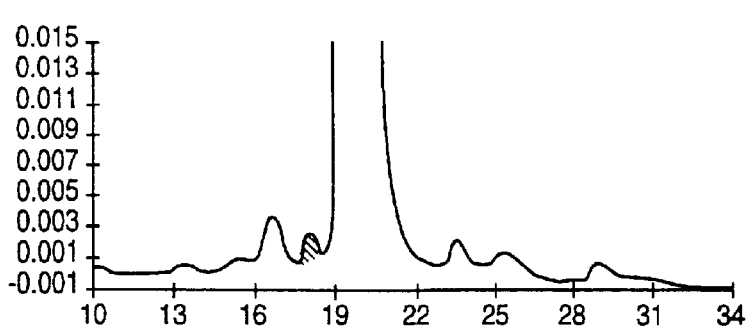

The results depicted in FIG. 5 show that greater than 98% of untreated glucagon runs as a single monomer with a retention time of about 20 minutes (FIG. 5A). Immediately after drying in glucose, there was a single peak of glycated glucagon (shaded) running immediately ahead of the monomer peak (FIG. 5B). Within 4 days at 60° C. in glucose the majority of the glucagon was destroyed by glycation and cross-linking (shaded, FIG. 5C). After 2 weeks storage in sucrose, a peak of glycated glucagon runs immediately ahead of the main monomer peak (shaded, FIG. 5D) even though no such peak was evident in the sample after drying.

These results indicate that in the case of glucose (a reducing sugar), the Schiffs base is formed during drying whereas in the case of sucrose (a non-reducing sugar), a Schiffs base is formed upon storage. As a non-reducing sugar, sucrose would not be expected to form a Schiffs base upon either drying or storage. This indicates that the Maillard reaction occurs with both reducing and non-reducing sugars, and thus the present invention is suitable for use with both reducing and non-reducing sugars. These results further indicate that, in the case of sucrose as an excipient, a reducing sugar is generated by hydrolysis that may be catalyzed by the substance being stored. Furthermore, the Schiffs base formation by the reducing sugar generated releases water which not only plasticizes the system but directly accelerates both further hydrolysis reactions and the Maillard cascade (see Example 5, below). Thus, in light of the results presented herein, the use of an inhibitor of the Maillard reaction is particularly useful in conjunction with a non-reducing sugar in dry storage of biological substances.

Example 5

The Effect of Water on Storage Stability

To investigate directly the effect of residual moisture on chemical reactivity, a model system containing lysine with two non-reducing excipients trehalose and sorbitol, dried and stored at 3 different defined residual water contents, was used. Chemical reactivity was ensured by spiking the drying mixtures with a 5% trace of glucose, and its reaction with the lysine was measured by the quantitation of the glucose remaining after storage at 50° C.

FIG. 6 shows the results obtained where solutions of 10% w/v lysine and 5% glucose in 85% trehalose (a) or 85% sorbitol (b) in water were freeze-dried with primary drying at −50° C. for 48 hr and secondary drying for a further 24 hr at 20° C. The desired water content was achieved by storage at 20° C. over anhydrous $P_2O_5$ followed by exposure to a saturated water vapor atmosphere for either O hr, 8 hr or 25 hr. The actual final water content of the samples was determined by thermogravimetry using a Kahn microbalance. FIG. 6 depicts the results as follows: a) (☐) 4.59% water, (◇) 15.09% water, (x) 22.89% water; and b) (☐) 5.42% water, (◇) 13.12% water, (x) 23.62% water.

Figure 6A:
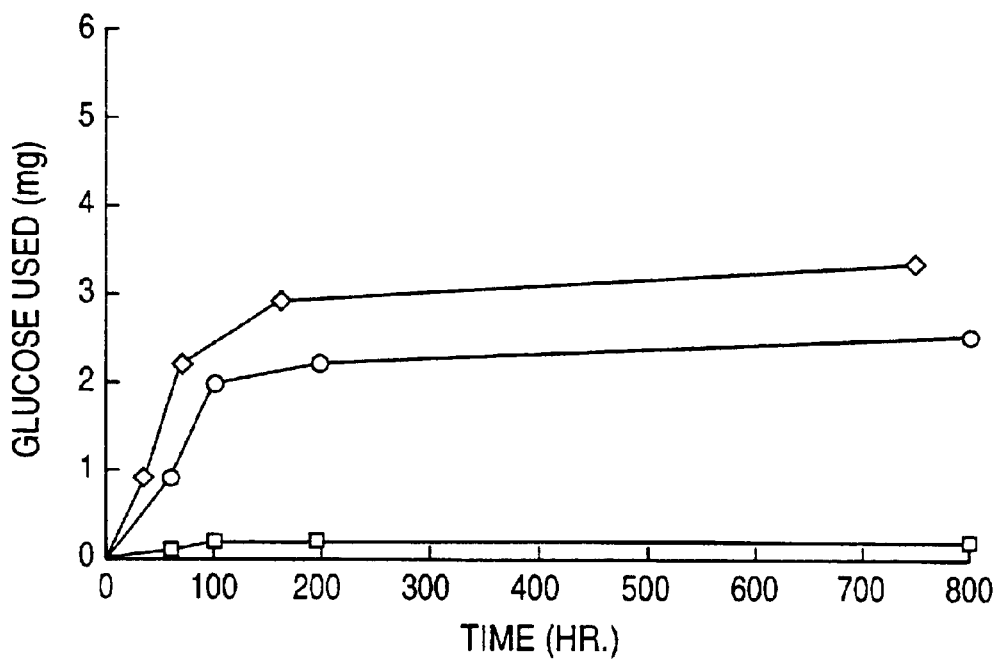
FIG. 6. Effect of residual water content on chemical reactions in model excipients.
Figure 6B:
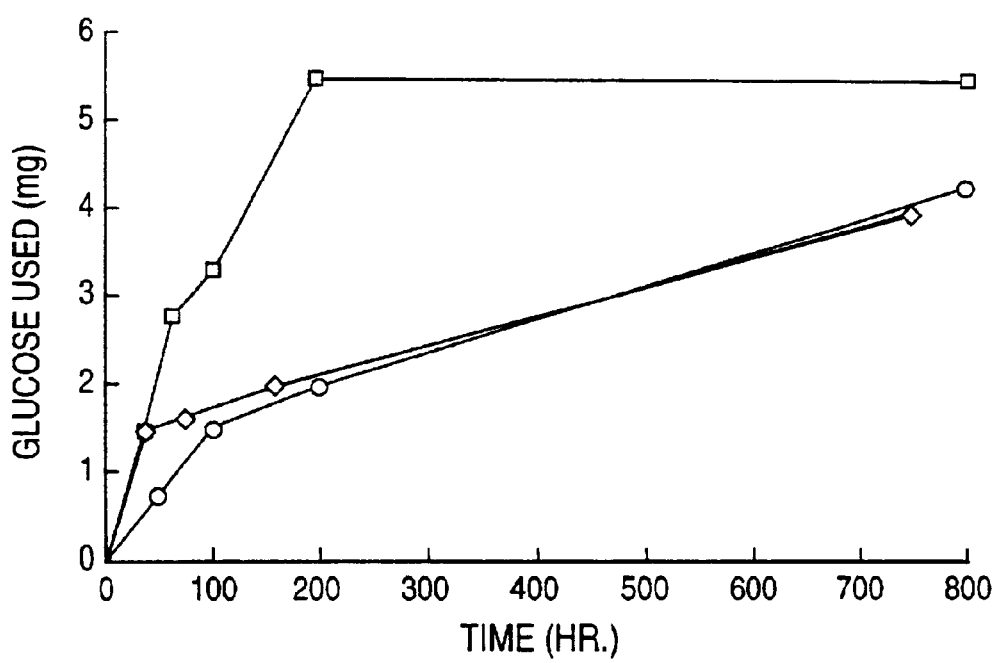

The results obtained indicate that in the trehalose samples, chemical reactivity was reduced as the residual water content decreased, and essentially no reactivity was observed at a water content of around 5% (FIG. 6a). In contrast, in the sorbitol samples, the chemical reactivity was accentuated under the driest conditions (FIG. 6b). The results show that Maillard-type reactions are extremely important during the storage of dried products, as these reactions are driven to completion in systems whether water activity is limiting.

Example 6

The Effect of a Noncompetitive Inhibitor of the Maillard Reaction

Bovine serum albumin was dried from solutions containing reducing sugars and incubated at 55° C. for 3 weeks, in the presence or absence of various concentrations of the Maillard reaction inhibitor aminoguanidine. The extent of the Maillard reaction was quantified spectrophotometrically at 277–290 nm by the formation of brown color.

The results obtained are shown in Table 3.

TABLE 3

| Sugar (25 mM) | Potential Inhibitor | Ratio Sugar: Inhibitor (molar basis) | Absorbance extent of browning |
|---|---|---|---|
| Glucose | None | | 0.709 |
| Glucose | aminoguanidine | 3:1 | 0.603 |
| Glucose | aminoguanidine | 2:1 | 0.205 |
| Glucose | aminoguanidine | 1:1 | 0.212 |
| Glucose | aminoguanidine | 1:2 | 0.211 |
| Glucose | aminoguanidine | 1:3 | 0.154 |
| None | aminoguanidine | 1:3 | 0.186 |
| Fructose | None | | 2.5 |
| Fructose | aminoguanidine | 1:3 | 0.173 |

The results obtained indicate that the addition of a Maillard reaction inhibitor to a protein formulation being dried, prevents the degradation of the dried protein product during storage at elevated temperatures.

Example 7

The effect of Competitive Inhibitors of the Maillard Reaction

In order to determine the effect of competitive inhibitors on reducing the effects of the Maillard reaction upon storage of dried compositions, the following experiment was performed. The results are presented in FIG. 7.

Figure 7:
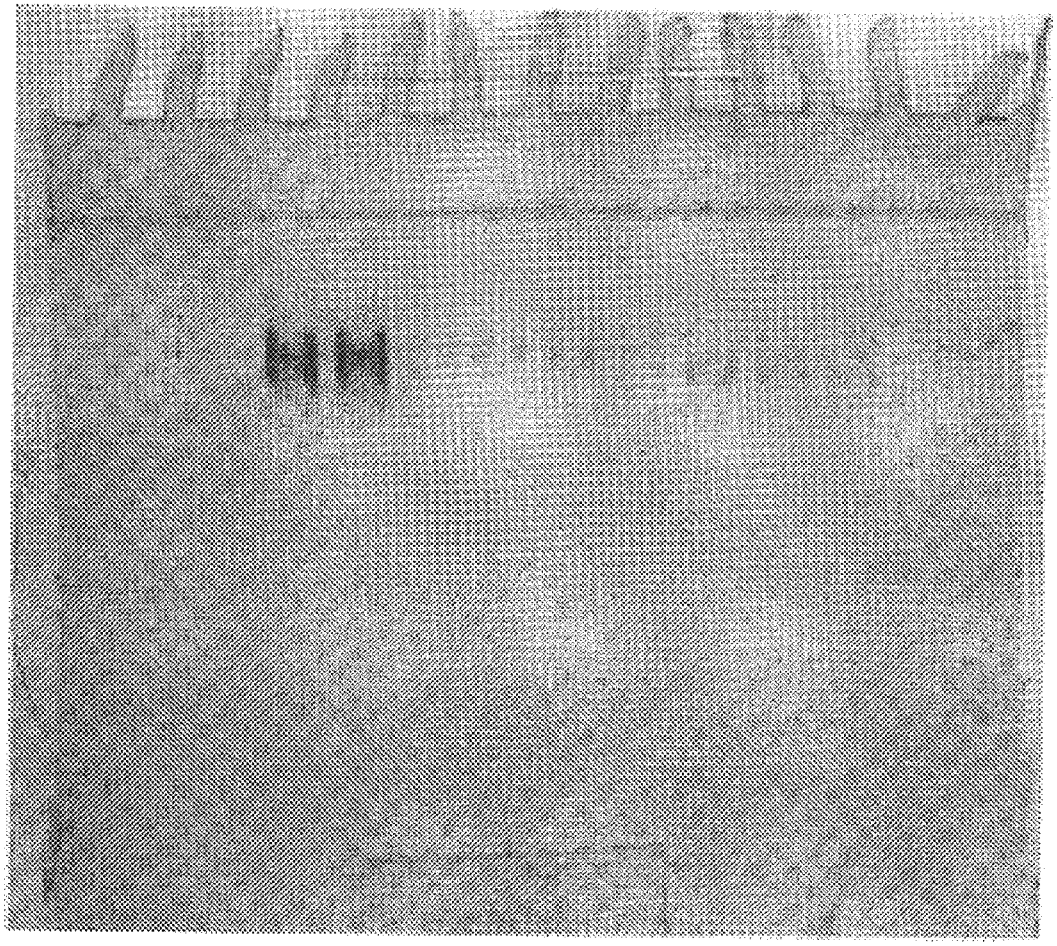
FIG. 7. Activity of alkaline phosphatase upon drying and storage in glucose and increasing amounts of lysine.

Alkaline phosphatase (0.25 mg/ml) was dried under vacuum (80 microns) at ambient temperature for 16 hours from a formulation containing 15% glucose as the carbohydrate excipient with either 0, 7.5, 15 and 25% lysine added as a competitive Maillard reaction inhibitor. The samples were stored for four days at 55° C. and assayed by running on a 10% polyacrylamide gel and stained for enzymatic activity using α-naphthyl acid phosphate and Fast Blue BB (1 mg/ml and 1.33 mg/ml, respectively, in 0.38 M Tris-HCl (pH 10.3) containing 0.5 mM $MgCl_2$) (FIG. 7, tracks 1–4, respectively). Controls run were enzyme in aqueous buffer and enzyme dried in trehalose (FIG. 7, lanes 8–9, respectively). Although only partial activity was recovered in the glucose plus lysine samples, these showed increased activity recovered with increasing concentration of added lysine. In the sample with glucose but with no added lysine, no enzymatic activity was recovered.

Thus, a competitive inhibitor of the Maillard reaction, when dried with a mixture of protein and carbohydrate, increases the stability of the protein during drying and storage of the dried product.

In conclusion, our results suggest that the Maillard reaction is an extremely important factor in determining the long term storage stability of dry protein formulations containing carbohydrates as stabilizing excipients. While not being bound by any one theory, this may be due to both the shift in the equilibrium of the initial amino-carbonyl condensation reaction towards the formation of the Schiffs base by the removal of water during drying and the acceleration of the subsequent reactions at low water activities. Lendl and Schleicher (1990) and Nursten (1986).

Although the foregoing invention has been described in some detail by way of illustration and example for purposes of understanding it will be apparent to those skilled in the art that certain changes and modifications may be practiced. Therefore, the description and examples should not be construed as limiting the scope of the invention, which is delineated by the appended claims.

What is claimed is:

1. A stabilized dry composition comprising a therapeutic agent susceptible to the Maillard reaction, containing free amino, imino or guanidino side chains, wherein said composition further comprises a reducing carbohydrate as a stabilizer for the therapeutic agent and an inhibitor of the Maillard reaction wherein the carbohydrate is present in an amount sufficient to stabilize the therapeutic agent and the inhibitor is present in an amount sufficient to substantially prevent condensation of the amino, imino, or guanidino side chains.

2. The composition according to claim 1 wherein the therapeutic agent is selected from the group consisting of lipids, proteins, peptides, hormones, synthetic peptides, D and L amino acid polymers, nucleic acids, and protein nucleic acid hybrids.

3. The composition according to claim 2 wherein the proteins are selected from the group consisting of enzymes, biopharmaceuticals, growth hormones, growth factors, monoclonal antibodies and cytokines.

4. The composition according to claim 1 wherein the carbohydrate is selected from the group consisting of glucose, maltose, lactose, maltulose, iso-maltulose and lactulose.

5. The composition according to claim 1 wherein the carbohydrate is physiologically acceptable.

6. The composition according to claim 1 wherein the inhibitor is competitive.

7. The composition according to claim 6 wherein the inhibitor is a molecule with at least one primary, secondary or tertiary amine group.

8. The composition according to claim 7 wherein the inhibitor is selected from the group consisting of at least one amino acid residue, a mixture of amino acid residues or short peptides comprised of amino acid residues.

9. The composition according to claim 1 wherein the inhibitor is noncompetitive.

10. The composition according to claim 9 wherein the inhibitor is selected from the group consisting of aminoguanidine derivatives, amphotericin B, 4-hydroxy-5,8-dioxoquinoline derivatives, 4,5,8-trihydroxyquinoline derivatives, 3-oxophenoxazine derivatives, 3-oxophenoxazine N-oxide, ascorbic acid tocopheryl phosphate diesters and salts thereof.

11. The composition according to claim 1 wherein the therapeutic agent is storage stable at 0° C.–80° C.

12. The composition according to claim 1 wherein the therapeutic agent is storage stable at 0° C.–65° C.

13. The composition according to claim 1 wherein the therapeutic agent is storage stable at 10° C.–60° C.

14. The composition according to claim 1 wherein the therapeutic agent is storage stable at 20° C.–50° C.

15. The composition according to claim 1 wherein the therapeutic agent is storage stable at above ambient temperature.

16. A stabilized dry composition comprising an enzyme or a monoclonal antibody susceptible to the Maillard reaction, containing free amino, imino or guanidino side chains, wherein said composition futher comprises a reducing carbohydrate as a stabilizer for the enzyme or monoclonal antibody and an inhibitor of thr Maillard reaction wherein the carbohydrate is present in an amount sufficient to stabilize the enzyme or monoclonal antibody and the inhibitor is present in an amount sufficient to substantially pervent condensation of the amino, imino, or guanidino side chains.

* * * * *

UNITED STATES PATENT AND TRADEMARK OFFICE
CERTIFICATE OF CORRECTION

PATENT NO. : 6,313,102 B1
DATED : November 6, 2001
INVENTOR(S) : Camilo Colaco, Bruce J. Roser, Shevanti Sen It is certified that error appears in the above-identified patent and that said Letters Patent is hereby corrected as shown below:

<u>Title page,</u>
Assignee, "Quardrant" should read -- Quadrant --.

<u>Column 16, claims 16,</u>
Line 15, "pervent" should read -- prevent --.

Signed and Sealed this

Nineteenth Day of March, 2002

Attest:

JAMES E. ROGAN
Director of the United States Patent and Trademark Office

Attesting Officer